US011154642B2

(12) United States Patent
Rizk et al.

(10) Patent No.: US 11,154,642 B2
(45) Date of Patent: Oct. 26, 2021

(54) MEDICAL IMPLANTS INCLUDING LAMINATES OF POLY-4-HYDROXYBUTYRATE AND COPOLYMERS THEREOF

(71) Applicant: Tepha, Inc., Lexington, MA (US)

(72) Inventors: Said Rizk, Windham, NH (US); David P. Martin, Arlington, MA (US); Fabio Felix, Foxborough, MA (US); Matthew Bernasconi, Norwood, MA (US); Bhavin Shah, Lowell, MA (US); Simon F. Williams, Sherborn, MA (US)

(73) Assignee: Tepha, Inc., Lexington, MA (US)

( * ) Notice: Subject to any disclaimer, the term of this patent is extended or adjusted under 35 U.S.C. 154(b) by 353 days.

(21) Appl. No.: 14/574,649

(22) Filed: Dec. 18, 2014

(65) Prior Publication Data

US 2015/0182670 A1 Jul. 2, 2015

Related U.S. Application Data

(60) Provisional application No. 61/920,870, filed on Dec. 26, 2013.

(51) Int. Cl.
| | |
|---|---|
| *A61L 31/06* | (2006.01) |
| *A61L 27/18* | (2006.01) |
| *A61L 31/14* | (2006.01) |
| *A61L 31/16* | (2006.01) |
| *B29C 43/28* | (2006.01) |
| *C08G 63/06* | (2006.01) |
| *B29K 67/00* | (2006.01) |
| *B29L 9/00* | (2006.01) |

(52) U.S. Cl.
CPC .............. *A61L 31/06* (2013.01); *A61L 27/18* (2013.01); *A61L 31/146* (2013.01); *A61L 31/16* (2013.01); *B29C 43/28* (2013.01); *C08G 63/06* (2013.01); *B29K 2067/04* (2013.01); *B29L 2009/00* (2013.01); *Y10T 428/1393* (2015.01); *Y10T 428/24322* (2015.01); *Y10T 428/249921* (2015.04); *Y10T 442/10* (2015.04); *Y10T 442/183* (2015.04); *Y10T 442/184* (2015.04)

(58) Field of Classification Search
CPC ........ A61L 27/18; A61L 31/06; A61L 31/146; A61L 31/16; C08L 67/04; B29C 43/28; B29K 2067/04; B29L 2009/00; C08G 63/06; Y10T 428/1393; Y10T 428/24322; Y10T 428/249921; Y10T 442/10; Y10T 442/183; Y10T 442/184

See application file for complete search history.

(56) References Cited

U.S. PATENT DOCUMENTS

| | | | |
|---|---|---|---|
| 5,811,272 A | 9/1998 | Snell | |
| 5,876,550 A * | 3/1999 | Feygin | ..................... B29C 41/36 156/264 |
| 6,245,537 B1 | 6/2001 | Williams | |
| 6,316,262 B1 | 11/2001 | Huisman | |
| 6,323,010 B1 | 11/2001 | Skraly | |
| 6,548,569 B1 | 4/2003 | Williams | |
| 6,555,123 B2 | 4/2003 | Williams | |
| 6,585,994 B2 | 7/2003 | Williams | |
| 6,610,764 B1 | 8/2003 | Martin | |
| 6,623,748 B2 | 9/2003 | Clokie | |
| 6,828,357 B1 | 12/2004 | Martin | |
| 6,838,493 B2 | 1/2005 | Williams | |
| 6,867,247 B2 | 3/2005 | Williams | |
| 6,867,248 B1 | 3/2005 | Martin | |
| 6,878,758 B2 | 4/2005 | Signer | |
| 7,025,980 B1 | 4/2006 | Williams | |
| 7,179,883 B2 | 2/2007 | Williams | |
| 7,244,442 B2 | 7/2007 | Williams | |
| 7,268,205 B2 | 9/2007 | Williams | |
| 7,553,923 B2 * | 6/2009 | Williams | ................... A61F 2/07 264/176.1 |
| 7,618,448 B2 | 11/2009 | Schmitz | |

(Continued)

FOREIGN PATENT DOCUMENTS

| | | | |
|---|---|---|---|
| EP | 2647682 | 10/2013 | |
| EP | 2647682 A1 * | 10/2013 | ............ C09J 167/04 |

(Continued)

OTHER PUBLICATIONS

Nettles, Conference paper, NASA STI, Oct. 2012 (Year: 2012).*
Virmani et al. J. Vasc. Interv. Radiol. Apr. 1999;10(4):445-456 (Year: 1999).*
Levine et al., Material Science, 2009. (Year: 2009).*
Hori, et al., "Chemical synthesis of high Molecular weight poly(3-hydroxybutyrate-co-4-hydroxybutyrate)", Polymer, 36:4703-5 (1995).
Houk, et al., "Why delta-valerolactone polymerizes and gamma-butyrolactone does not", J. Org. Chem., 73 (7), 2674-8 (2008).
Martin, et al., "Medical applications of poly-4-hydroxybutyrate: a strong flexible absorbable biomaterial", Biochem. Eng. J., 16:97-105 (2003).

(Continued)

*Primary Examiner* — Jean P Cornet
(74) *Attorney, Agent, or Firm* — Wolf, Greenfield & Sacks, P.C.

(57) ABSTRACT

Methods to produce laminates including layers of constructs made from P4HB and copolymers thereof have been developed. These laminates may be used as medical implants, or further processed to make medical implants. The laminates are produced at a temperature equal to or greater than the softening points of the P4HB or copolymers thereof. The layers may include oriented forms of the constructs. Orientation can be preserved during lamination so that the laminate is also oriented, when the laminates are formed at temperatures less than the de-orientation temperatures of the layers. The laminate layers may include, for example, films, textiles, including woven, knitted, braided and non-woven textiles, foams, thermoforms, and fibers. The laminates preferably include one or more oriented P4HB films.

13 Claims, No Drawings

(56) References Cited

U.S. PATENT DOCUMENTS

| | | | |
|---|---|---|---|
| 7,641,825 B2 | 1/2010 | Rizk | |
| 7,678,444 B2 * | 3/2010 | Tedford, Jr. | B32B 1/02 |
| | | | 264/173.11 |
| 7,943,683 B2 * | 5/2011 | Rizk | B29C 55/12 |
| | | | 523/113 |
| 8,016,883 B2 | 9/2011 | Coleman | |
| 8,034,270 B2 | 10/2011 | Martin | |
| 8,039,237 B2 | 10/2011 | Martin | |
| 8,231,889 B2 | 7/2012 | Williams | |
| 8,287,909 B2 | 10/2012 | Martin | |
| 2005/0060020 A1 * | 3/2005 | Jenson | A61F 2/07 |
| | | | 623/1.13 |
| 2007/0182041 A1 | 8/2007 | Rizk | |
| 2008/0132602 A1 | 6/2008 | Rizk | |
| 2009/0274920 A1 | 11/2009 | Li | |
| 2010/0330382 A1 * | 12/2010 | Dou | B32B 27/36 |
| | | | 428/457 |
| 2012/0253472 A1 * | 10/2012 | Priewe | A61L 27/14 |
| | | | 623/23.72 |
| 2013/0046346 A1 * | 2/2013 | Thorwarth | A61F 2/02 |
| | | | 606/281 |
| 2013/0309166 A1 | 11/2013 | Rizk | |
| 2014/0030422 A1 | 1/2014 | Trollsas | |

FOREIGN PATENT DOCUMENTS

| | | |
|---|---|---|
| WO | 9932536 | 7/1999 |
| WO | 0056376 | 9/2000 |
| WO | 2004006808 | 7/2004 |
| WO | 2007092417 | 8/2007 |
| WO | 2008070428 | 6/2008 |
| WO | 2011119742 | 9/2011 |
| WO | 2011159784 | 12/2011 |
| WO | 2012048105 | 4/2012 |
| WO | 2012064526 | 5/2012 |
| WO | 2012142100 | 10/2012 |

OTHER PUBLICATIONS

Moore, et al., "Chemosynthesis of bioresorbable poly(gamma-butyrolactone) by ring-opening polymerisation: a review", Biomaterials, 26:3771-82 (2005).

Steinbüchel, et al., "Diversity of bacterial-polyhydroxyalkanoic acids", FEMS Microbial. Lett., 128:219-28 (1995).

Williams, et al., "Applications of PHA\s in medicine and pharmacy", Polyesters, III, 4:91-127 (2002).

International Search Report for PCT/US2014/071073 dated Mar. 19, 2015.

Williams, et al., "poly-4-hydroxybutyrate (P4HB): a new generation of resorbabale medical devices for tissue repair and regeneration ", Biomed. Tech. (Berl). 58(5):439-452 (2013).

International Search Report PCT application PCT/US2014/051922 dated Apr. 15, 2015.

* cited by examiner

MEDICAL IMPLANTS INCLUDING LAMINATES OF POLY-4-HYDROXYBUTYRATE AND COPOLYMERS THEREOF

CROSS-REFERENCE TO RELATED APPLICATIONS

This application claims the benefit of priority to U.S. Ser. No. 61/920,970, filed on Dec. 26, 2013, the disclosure of which is incorporated herein by reference.

FIELD OF THE INVENTION

The present invention generally relates to laminate structures of poly-4-hydroxybutyrate and copolymers thereof, the compositions and structures used to produce these laminates, and the processes used to produce these laminates.

BACKGROUND OF THE INVENTION

Many applications require relatively thin structures with a lot of strength and less flexibility. Laminates were developed as a means to make a stronger material from thin sheets or layers of materials. Laminates are typically formed by layering two or more sheets together, then bonding them with heat, adhesive, pressure or a combination thereof.

There is a need for laminates of P4HB and copolymers, and methods to prepare layers of P4HB and copolymers thereof so that they will bond in a lamination processes. Laminates are formed of multiple layers of material which are then glued or bonded together to form a stronger less flexible material.

It is therefore an object of the present invention to provide layers of constructs including P4HB and copolymers thereof that can be laminated.

It is another object of the present invention to provide a means of laminating layers of constructs which include P4HB and copolymers thereof.

It is still another object of the present invention to provide laminates of layers of P4HB and copolymers thereof with enhanced mechanical properties and controlled degradation profiles that can be used in medical applications.

SUMMARY OF THE INVENTION

Laminates and compositions of layers of P4HB and copolymers thereof that can be laminated have been developed. Laminated layers of constructs which include P4HB or copolymers thereof have also been developed. The laminate layers may form constructs such as films, textiles, including woven, knitted, braided and non-woven textiles, foams, thermoforms, and fibers. These constructs may be oriented in one or more directions. In a preferred embodiment, the laminate includes one or more oriented P4HB films, and in a particularly preferred embodiment, the film is perforated to make an implant. The laminates make it possible to form thick biaxially oriented films of P4HB, despite the polymer stretching many multiples of its own length. For example, forming a 200 µm biaxially oriented film starting with an 8-10 mm thick unoriented sheet and stretching it seven times its original length is technically much more difficult than using processing equipment to make a 20 µm biaxially oriented film, stacking ten P4HB film layers, and laminating to produce a 200 µm biaxially oriented film.

Methods of producing laminates of layers of constructs including P4HB and copolymers thereof have been developed. The laminates are produced at a temperature equal to or greater than the softening points of P4HB and copolymers thereof, typically between 52 and 85° C. for P4HB. For the copolymers the range is wider because the melting points range from about 40° C. to nearly 180° C., typically between 35 and 200° C. for the P4HB copolymers. In one embodiment, the layers include oriented forms of P4HB or copolymers thereof, and the laminates are formed at temperatures less than the de-orientation temperatures of the layers, i.e., less than 85° C.

The P4HB laminates have enhanced mechanical properties and controlled degradation profiles and can be used in medical applications. The laminates can be used in many types of implant applications and surgeries including wound management, hernia repair, anti-adhesion devices, tissue engineering scaffolds, plastic and reconstructive surgery including mastopexy and facelifts, drug delivery, pelvic floor and bladder reconstruction, nerve repair, orthopedic surgery, stenting, periodontal surgery, oral surgery, and vascular and cardiovascular surgery. In some embodiments, the implant has one or more of the following properties: tensile strength that is greater than 45 MPa, tensile modulus that is greater than 55 MPa, burst strength that is greater than 1 N, and elongation to break that is between 10% and 500%.

DETAILED DESCRIPTION OF THE INVENTION

Methods have been developed to prepare laminates from layers of constructs including P4HB and copolymers thereof, at temperatures at or above the softening point of P4HB. These methods do not result in compression of the layers during lamination. Advantageously, layers of P4HB and copolymers thereof can be laminated without the use of sealing layers. A sealant (glue) is often used to make sure the surfaces of the films stick to each other. The sealants make the film tacky. It appears that heating the P4HB films above the softening point is sufficient to provide a good bond between the surfaces without the need to use a sealant. Presumably heating causes the P4HB film surfaces to become slightly tacky, allowing them to stick to each other.

The methods disclosed herein are based on the discovery that oriented layers of P4HB and copolymers thereof can be laminated without significant loss of orientation at temperatures between their softening temperatures and de-orientation temperatures even though there is a narrow band between these two temperatures. Furthermore, if the oriented layers have been annealed, the layers can be laminated at a temperature between the softening temperature of the polymer or copolymer and a temperature that is 5° C. less than the annealing temperature of the polymer or copolymer.

The methods described herein outline how P4HB and copolymers thereof can be laminated, including how layers of constructs including P4HB and copolymer materials can be sealed to each other or to other layers made from dissimilar materials; the properties of the constructs that can be laminated; the process conditions necessary to laminate layers of the constructs, including conditions that prevent de-orientation of oriented layers of P4HB and copolymers thereof and prevent the layers from being compressed; the stability of the layers during lamination, and processing conditions that prevent loss of intrinsic viscosity. The laminates formed from layers of constructs made from P4HB and copolymers thereof may be used as biocompatible implants, or may be converted to biocompatible implants through further processing.

I. Definitions

"Bioactive agent" is used herein to refer to therapeutic, prophylactic, and/or diagnostic agents. It includes without limitation physiologically or pharmacologically active substances that act locally or systemically in the body. A biologically active agent is a substance used for, for example, the treatment, prevention, diagnosis, cure, or mitigation of disease or disorder, a substance that affects the structure or function of the body, or pro-drugs, which become biologically active or more active after they have been placed in a predetermined physiological environment. Bioactive agents include biologically, physiologically, or pharmacologically active substances that act locally or systemically in the human or animal body. Examples can include, but are not limited to, small-molecule drugs, peptides, proteins, antibodies, sugars, polysaccharides, nucleotides, oligonucleotides, hyaluronic acid and derivatives thereof, aptamers, siRNA, nucleic acids, and combinations thereof. "Bioactive agent" includes a single such agent and is also intended to include a plurality.

"Bioceramic" means a ceramic suitable for use or replacement in the human body.

"Biocompatible" as generally used herein means the biological response to the material or device being appropriate for the device's intended application in vivo. Any metabolites of these materials should also be biocompatible.

"Blend" as generally used herein means a physical combination of different polymers, as opposed to a copolymer including two or more different monomers.

"Burst strength" as used herein is determined, unless otherwise specified, according to ASTM D6797-02 (Standard Test Method for Bursting Strength of Fabrics Constant-Rate-of-Extension (CRE) Ball Burst Test) at ambient conditions using a ball burst fixture with either a ⅜ inch ball or 1 inch ball, as described in the examples.

"Ceramic" means an inorganic, nonmetallic solid prepared by the action of heat and subsequent cooling.

"Copolymers of poly-4-hydroxybutyrate" as generally used herein means any polymer of 4-hydroxybutyrate with one or more different hydroxy acid units. Examples include, but are not limited to, copolymers of 4-hydroxybutyrate with 3-hydroxybutyrate, 2-hydroxybutyrate, lactic acid, and glycolic acid. Copolymers of poly-4-hydroxybutyrate include copolymers containing naturally occurring ratios of carbon, hydrogen, and oxygen isotopes, as well as copolymers that have been isotopically enriched in an isotope of carbon, hydrogen or oxygen. For example, the copolymers include one or more fully or partially deuterated 4-hydroxybutyrate monomers.

"Film" as generally used herein has a thickness of less than 10 mm.

"Implant" as generally used herein include medical devices that are used in vivo as well as those that contact the surface of the body or are inserted into any orifice of the body.

"Lamination" as used herein refers to a method for bonding together two or more layers made of the same or different materials. The materials may also have the same or different physical structures. During lamination there should not be any significant compression of the individual layers.

A "laminate" typically refers to devices or structures including multiple layers fixed together to form a hard, flat, or flexible material. These may be press bonded or bound by adhesive, or a combination thereof. Merely gluing two or more layers of materials together does not make a laminate.

"Molecular weight" as used herein, unless otherwise specified, refers to the weight average molecular weight (Mw), not the number average molecular weight (Mn), and is measured by GPC relative to polystyrene.

"Poly-4-hydroxybutyrate" as generally used herein means a homopolymer of 4-hydroxybutyrate units. It may be referred to herein as P4HB or TephaFLEX® biomaterial (manufactured by Tepha, Inc., Lexington, Mass.). Poly-4-hydroxybutyrate includes the monomer units with naturally occurring ratios of carbon, hydrogen and oxygen isotopes, as well as monomer units with specific quantities of these isotopes, i.e. that have been isotopically enriched. For example, the homopolymers may include one or more monomers that have been fully or partially deuterated at any position in the monomer.

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body, whether degradation is due mainly to hydrolysis or mediated by metabolic processes.

"Sheet" as generally used herein has a thickness of 10 mm or more.

"Softening Point" as used herein means the Vicat softening point determined according to test method ASTM D1525-09. The softening point is measured as the temperature at which a polymer is penetrated to a depth of 1 mm by a flat-ended needle with a 1 sq. mm circular or square cross-section under a load of 9.81 N.

II. Compositions

The processes described herein can be used to make laminates including P4HB polymers, copolymers and blends thereof, or blends of P4HB polymers/copolymers with other absorbable polymers.

The P4HB homopolymer and copolymers may be isotopically enriched in any manner. Examples of P4HB copolymers include copolymers of 4-hydroxybutyrate with 3-hydroxybutyrate, and with 2-hydroxy acids such as glycolic acid and lactic acid monomers. In a particularly preferred embodiment, the P4HB and copolymers thereof have intrinsic viscosities of 0.8 to 3.2 dl/g. The intrinsic viscosity of the P4HB and copolymers thereof may be determined using an Agilent 1100 Series HPLC equipped with an Agilent triple detector system (Agilent 390-LC Multi Detector Suite). The triple detector is equipped with a laser light scattering (LS) detector, a refractive index (RI) detector and a viscosity (Vis) detector. Samples of polymer may be prepared at 1 mg/ml in chloroform, and 100 μl of these solutions injected onto a Polymer Labs, PLgel column (5 micron, mixed C, 300×7.5 mm), and eluted at 1 ml/min. Intrinsic viscosity values may be determined using the Cirrus™ GPC/Multi Detector Software.

In some embodiments, the laminates may incorporate reinforcing elements, for example, resorbable biocompatible fibers and other additives, including, but not limited to, nucleating agents and/or plasticizers.

A. P4HB Polymers and Co-polymers for Lamination

P4HB and copolymers thereof belongs to a larger class of materials called polyhydroxyalkanoates (PHAs) that are produced by numerous microorganisms (see, for example, Steinbüchel A., et al. Diversity of Bacterial Polyhydroxyalkanoic Acids, *FEMS Microbial. Lett.,* 128:219-228 (1995)). In nature these polyesters are produced as storage granules inside cells, and serve to regulate energy metabolism. They are also of commercial interest because of their thermoplastic properties, biodegradability and relative ease of production.

Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Lexington, Mass.). P4HB homopolymer can be obtained from Tepha, Inc. of Lexington, Mass., USA. Copolymers of P4HB include 4-hydroxybutyrate with one or more hydroxyacid monomers. Poly-4-hydroxybutyrate (P4HB, TephaFLEX® biomaterial) is a strong, pliable thermoplastic polyester that, despite its biosynthetic route, has a relatively simple structure.

Chemical synthesis of P4HB has been attempted, but it has been impossible to produce the polymer with a sufficiently high molecular weight that is necessary for most applications, including melt processing (see Hori, et al., *Polymer* 36:4703-4705 (1995); Houk, et al., *J. Org. Chem.,* 73 (7):2674-2678 (2008); and Moore, et al., *Biomaterials,* 26:3771-3782 (2005)). In fact, it has been calculated to be thermodynamically impossible to chemically synthesize a high molecular weight homopolymer under normal conditions (Moore, et al., *Biomaterials* 26:3771-3782 (2005)). Chemical synthesis of P4HB instead yields short chain oily oligomers that lack the desirable thermoplastic properties of the high molecular weight P4HB polymers produced by biosynthetic methods.

It should be noted that the literature commonly refers to another polyhydroxyalkanoate, poly-3-hydroxybutyrate (P3HB), simply as polyhydroxybutyrate (PHB) (see Section 2 of Moore, et al., *Biomaterials* 26:3771-3782 (2005)). PHB has entirely different properties to P4HB. For example, PHB has a melting point of 180° C. versus a melting point of about 61° C. for P4HB. The polymers also have substantially different glass transition temperatures and mechanical properties. PHB is a relatively hard brittle polymer with an extension to break of just a few percent, whereas P4HB is a strong extensible polymer with an extension to break of about 1000%. Substantially different conditions are required to process these two polymers, and the resulting products have substantially different properties.

U.S. Pat. Nos. 6,245,537, 6,623,748, 7,244,442, and 8,231,889 describe methods of making PHAs with little to no endotoxin, which are suitable for medical applications. U.S. Pat. Nos. 6,548,569, 6,838,493, 6,867,247, 7,268,205, 7,179,883, 7,268,205, 7,553,923, 7,618,448 and 7,641,825 and WO 2012/064526 describe use of PHAs to make medical devices. Copolymers of P4HB include 4-hydroxybutyrate copolymerized with 3-hydroxybutyrate or glycolic acid (U.S. Pat. No. 8,039,237 to Martin and Skraly, U.S. Pat. No. 6,316,262 to Huisman et al., and U.S. Pat. No. 6,323,010 to Skraly et al.). Methods to control molecular weight of PHA polymers have been disclosed by U.S. Pat. No. 5,811,272 to Snell et al.

In some embodiments, the press laminates described herein have controlled degradation rates. PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. In these embodiments, a PHA with controlled degradation rates is selected to make the construct to be laminated.

(i) Additional Non-4HB Polymers

The compositions for lamination may include the P4HB homopolymer or copolymer blended with other absorbable polymers. Other absorbable polymers include, but are not limited to, poly(lactides); poly(glycolides); poly(lactide-co-glycolides); poly(lactic acid); poly(glycolic acid); poly(lactic acid-co-glycolic acids); polycaprolactones; poly(orthoesters); polyanhydrides; poly(phosphazenes); polyhydroxyalkanoates [including PHB, poly-3-hydroxybutyrate-co-3-hydroxyvalerate (PHBV)]; synthetically or biologically prepared polyesters (including polyesters with one or more of the following monomeric units: glycolic, lactic; trimethylene carbonate, p-dioxanone, or ϵ-caprolactone); poly(lactide-co-caprolactones); polycarbonates; tyrosine polycarbonates; polyamides (including synthetic and natural polyamides, polypeptides, and poly(amino acids)); polyesteramides; poly(dioxanones); poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); chitin; chitosan; modified chitosan; collagen; silk; biocompatible polysaccharides; biocompatible copolymers (including block copolymers or random copolymers); hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide, or polycaprolcatone or combinations thereof.

(ii) Reinforcing Elements

If desired, the compositions for lamination may also incorporate reinforcing elements to improve the properties of the laminates. Such reinforcing elements may be used to improve properties such as tensile strength, burst strength and Young's modulus. In a preferred embodiment, the reinforcing elements are resorbable biocompatible fibers. In a particularly preferred embodiment, the reinforcing elements are fibers of polymers with monomers selected from glycolic acid, lactic acid, trimethylene carbonate, p-dioxanone, 4-hydroxybutyrate and ϵ-caprolactone.

B. Incorporation of Additives into Compositions of P4HB and Copolymers Thereof

Certain additives may be incorporated into P4HB, copolymers and blends thereof prior to converting these compositions into layers for lamination. Preferably, these additives are incorporated during the compounding process to produce pellets that can be subsequently processed into layers for lamination. For example, the pellets may be extruded into film layers or melt-blown to provide non-woven layers. In another embodiment, these additives may be incorporated using a solution-based process, for example, layers of film may be cast from solutions containing P4HB and additives, or nonwovens electrospun from the solutions. The additives preferably are biocompatible and resorbable.

Additives which may be added into the laminates include, but are not limited to, nucleating agents contrast agents, radiopaque markers and radioactive substances, ceramics and/or plasticizers. The additives are added in sufficient quantity to produce the desired result. In general, the additives are added in amounts of up to 20% by weight.

Nucleating agents may be incorporated to increase the rate of crystallization of the P4HB homopolymer, copolymer or blend. Such agents may be used to improve the mechanical properties of the layers, resulting laminates, and to reduce cycle times. Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated into the compositions for preparing layers for lamination include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

Useful ceramics include bioceramics preferably resorbable bioceramics. Examples of resorbable bioceramics that can be incorporated into the constructs (to be laminated) containing P4HB homopolymer, copolymer and blends thereof include tricalcium phosphate (α and β forms of tricalcium phosphate (TCP)—with a nominal composition of $Ca_3(PO_4)_2$), biphasic calcium phosphate (BCP), hydroxylapatite, calcium sulfate, calcium carbonate, and other calcium phosphate salt-based bioceramics. Bio-active glasses may also be used. Bioactive glasses include bioactive glasses composed of $SiO_2$, $Na_2O$, $CaO$ and $P_2O_5$ in specific proportions. The resorbable bioceramics may be included in a size distribution ranging from nanoparticles to microparticles, preferably at particle sizes of less than 100 microns. In a particularly preferred embodiment of the invention, the P4HB blends include β-TCP, α-TCP or a combination thereof.

C. Incorporation of Therapeutic, Prophylactic, Neutraceutical, or Diagnostic Agents into Compositions Of P4HB Polymer and Copolymers Thereof If desired, the P4HB homopolymer and copolymers thereof used to make the laminates may incorporate active agents such as therapeutic, prophylactic, neutraceutical or diagnostic agents. These agents may be added during the formulation process, during pelletization, or may be added later to the layers or laminates.

Examples of useful bioactive agents include, but are not limited to, small-molecule drugs, proteins, peptides, sugars, carbohydrates, lipids, nucleic acids, organic or inorganic biomaterials such as hydroxyapatite, calcium, chitosan or alginate, and combinations thereof. Representative therapeutics include anti-inflammatory agents, immunomodulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, signaling ligands, platelet rich plasma, anesthetics, hormones, antibodies, growth factors, fibronectin, laminin, vitronectin, integrins, antibiotics, steroids, hydroxyapatite, silver particles, vitamins, chitosan and derivatives thereof, alginate and derivatives thereof, collagen, hyaluronic acid and derivatives thereof. Representative nucleic acid molecules include antisense molecules, aptamers, siRNA, nucleic acids, and combinations thereof.

II. Methods of Preparing Layers of Constructs Including P4HB and Copolymers Thereof for Lamination The P4HB homopolymer, copolymer or blend may be converted into constructs, which are laminated as layers, by any suitable method. Suitable constructs for lamination include film, sheet, woven textiles, non-woven textiles, knitted textiles, fibrous layers, braids, thermoforms, fiber-reinforced layers, foams, molded layers, tubes, embossed layers, adhesive layers, dyed layers, and pultruded forms. The layers may be non-porous or porous (with pores of the same sizes or different sizes and placed in a regular or non-regular pattern).

The layers may vary in their shapes, for example, layers may be rectangular, square, diamond, circular, oval, or of an irregular nature. The layers may be of uniform thickness, or may vary in thickness, for example from one side of a layer to another.

The films and sheets may be un-oriented, partially or fully oriented in one or more directions. In a preferred method the film or sheet is extruded either directly from a powder or granular form of the polymer or copolymer composition, or even more preferably is extruded from pellets. Films and sheets may be produced by methods such as melt extrusion, compression molding, injection molding, and solvent casting. Textile layers may be produced by melt or solvent processing methods, including, for example, melt-blowing as disclosed by U.S. Pat. No. 8,287,909 to Martin et al., dry spinning as disclosed by WO 2011159784 to Cahil et al., electrospinning, spunbonding, and by carding of staple fibers. The fibers in the textile structures may be unoriented or partially or fully oriented, and they may be annealed.

Powder, granules or pellets including P4HB homopolymer, copolymer or blends thereof are preferably dried prior to melt extrusion in order to limit the loss of intrinsic viscosity of the polymer during film and sheet formation. The specific extent of drying necessary depends on the loss of intrinsic viscosity that can be tolerated for a particular application. In one embodiment, the polymer or blend to be melt-extruded is dried such that the moisture content of the polymer or blend is no greater than 0.5% by weight as measured gravimetrically, and more preferably no greater than 0.05% by weight. The polymer or blend may be dried in vacuo. For example, the polymer or blend is dried in a vacuum chamber under a vacuum of at least 10 mbar, more preferably of at least 0.8 mbar, to a moisture content of less than 0.03% by weight. Elevated temperatures below the melting point of the polymer pellets may also be used in the drying process. Alternatively, the polymer may be dried by extraction into a solvent and re-precipitation, or with the use of desiccants.

The moisture content of samples of the P4HB homopolymer, copolymer or blends thereof may be determined using a VaporPro Moisture Analyzer from Arizona Instruments, or similar instrument, as follows. Samples should be transferred to test vials in a low humidity environment (<5% RH) to minimize pickup of ambient moisture. Samples (1 g) can then be heated to 120° C. under a purge of dry nitrogen. The moisture content of the purge gas is determined by the Vapor Pro and reported as a % of the sample weight.

Melt Extrusion

Melt-extrusion may be used to prepare films or sheets of P4HB homopolymer, copolymer or blends thereof, suitable for lamination, using barrel and T-die temperatures of 80 to 250° C., and more preferably 100 to 220° C. In a preferred embodiment, films or sheets of molten P4HB homopolymer, copolymer or blends exiting the T-die are chilled by casting over one or more rotating cylindrical cast rollers with a surface temperature of 5 to 100° C., and more preferably 5 to 20° C. The solidified film or sheet may then be wound up in a take up step to collect the film or sheet. Films and sheets of P4HB with different thicknesses can be produced using this process by adjusting the gap of the T-die slit, and altering the polymer flow rate and cast roll speed.

Films and sheets of P4HB homopolymer, copolymer or blends thereof suitable for lamination may also be prepared by extrusion using an inflation method wherein an inflation molding circular die is used instead of a T-die to extrude cylindrical film or sheet. After exiting the circular die, the molten cylindrical film or sheet is cooled by blowing it up using cold air blown from the central portion of the circular die. Once the polymer has solidified, the film or sheet may be collected using a take-up machine. Films and sheets of P4HB homopolymer, copolymer or blends thereof with different thicknesses can be produced by changing the gap of the inflation die slit, as well as altering the polymer flow rate, cooling air pressure, temperature of the air, and the take-up speed.

Compression Molding

In addition to melt extruding and blowing films and sheets of P4HB homopolymer, copolymer or blends thereof, suitable films and sheets for lamination may also be made by compression molding. In one embodiment, compositions include a P4HB homopolymer, copolymer or blends thereof may be pressed into films and sheets using a Carver hydraulic press. In a preferred embodiment, compositions including P4HB powder, granules or pellets can be pressed into films and sheets by heating the platens of the press to 115° C., and pressing the P4HB composition between two sheets of mylar using metal spacers. After pressing, the film or sheet is removed from the press, allowed to cool and solidify, and removed from the Mylar backing material. The thickness of the metal spaces may be adjusted in order to produce films and sheets of the desired thickness.

Solvent Casting

Films and sheets of a P4HB homopolymer, copolymer or blends thereof, suitable for lamination, can also be prepared by solvent casting. In a preferred embodiment, a solution of P4HB can be prepared by dissolving the P4HB polymer in a solvent at a concentration of 10-15 wt/vol %, or at a concentration such that the P4HB solution has a viscosity of 400 to 7,400 cP. Suitable solvents include tetrahydrofuran, 1,4-dioxane, acetone, chloroform, and methylene chloride. The polymer solution is pumped through a slot die onto a moving web such as, for example, an aluminum foil. The distance traveled by the moving web before being taken up on a collection roller is adjusted to ensure evaporation of the solvent, and one or more air-drying zones, preferably with elevated temperatures, may be used to speed up solvent evaporation. In one embodiment, the slot die has a width of 150 mm and a 400 μm die gap, and the web speed is 0.5 m/min with the web traveling 5 m before the film is collected on a final roll. The pump speed, die gap and width, polymer concentration, and web speed may all be varied to produce films and sheets of P4HB homopolymer, copolymer or blends thereof of the desired thickness and widths.

Orienting Films/Sheets

The films and sheets of P4HB homopolymer, copolymer or blends thereof, to be used as layers for lamination, may be oriented. Suitable methods to orient films and sheets of P4HB homopolymer, copolymer or blends thereof include roll stretching and/or stretching with a tenter frame. In a preferred embodiment, the films and sheets are stretched at a temperature between room temperature and 150° C., more preferably at 40 to 80° C., and with a stretch ratio of 0.25 to 15. The films and sheets may be monoaxially stretched to form monoaxially-oriented films and sheets, consecutively stretched in biaxial directions to form biaxially oriented films and sheets, or simultaneously biaxially stretched to form plane-oriented films and sheets. Suitable equipment to orient the films and sheets includes the Bruckner Karo IV stretching machine.

In a preferred embodiment, the oriented films and sheets can be heat set or annealed to minimize or eliminate shrinking during lamination. The films and sheets may be heat set by restraining the films and sheets at the desired stretched dimensions, and heating to a temperature of less than 60° C., and more preferably 35 to 55° C. In a preferred embodiment, the layers are heated in a water bath while maintaining the layer in a stretched condition. The films or sheets can be porous or fibrillated. These films or sheets can be made porous by mechanical or laser drilling, punching or any similar method to create pores in the film or sheet.

In addition to the methods described above, the layers of constructs containing P4HB or copolymers thereof may be derived from the co-extrusion of a P4HB homopolymer, copolymer or blends thereof.

III. Lamination of Layers of P4HB and Copolymers Thereof

Layers of constructs including P4HB, copolymers and blends thereof can be laminated at temperatures at or above their softening temperatures without any significant loss of molecular weight, and without any significant compression of the layers. The softening temperature for P4HB is 51.9° C. The copolymer softening range is from 35 to 175° C. In contrast to the prior art which teaches the use of sealants in the manufacture of laminates to get good bonding between the film surfaces, no sealant is required to laminate P4HB films together, and get good bonding between the surfaces. After lamination it is not possible to peel away the films that were used to make the laminate.

The methods disclosed herein allow lamination of layers of P4HB, copolymers and blends thereof in oriented forms, such as uniaxially and biaxially oriented films and sheets, without loss of orientation at temperatures between their softening points and their de-orientation temperatures. Since there is no loss of orientation during lamination, and molecular weight is substantially maintained, good retention of mechanical properties can be achieved resulting in laminates of high tensile strength. Furthermore, because there is no loss of orientation during lamination, biaxially oriented laminates made from transparent or essentially transparent layers retain substantially these optical properties. Oriented laminates are essentially transparent whereas un-oriented laminates are opaque. Oriented laminates have slightly higher melting temperatures than un-oriented laminates. Oriented laminates have substantially higher tensile strength, and substantially lower elongation to break.

One or more films or sheets can be laminated together. The laminates may also be derived from layers of one or more textiles, for example, laminates including only textiles, or laminates made from both textile layers and other non-textile layers such as sheets or films. In one embodiment, one or more films or sheets is laminated with a textile layer. In another embodiment, one or more films or sheets is laminated with a monofilament mesh preferably made from P4HB, copolymer or blend thereof.

The laminates may also be derived from layers of one or more foams containing P4HB, copolymers and blends thereof, including laminates made only from foam layers, and laminates made from both foam layers and other non-foam layers, including, for example, one or more sheet or film layers. The foams may be open or closed cell foams, and may be produced by methods such as melt-foaming, thermal phase separation or particulate leaching techniques.

The laminates may be made using a variety of lamination techniques. The constructs to be laminated may be laminated by press lamination, for example, by stacking the layers in the desired manner, placing them in a press, and applying pressure and heat to the stack of layers to form the laminate. The layers are preferably placed between sheets of non-adherent material, such as sheets of polytetrafluroethylene ("PTFE"), to prevent the laminated layers from adhering to the platens of the press.

The layers to be laminated are heated to at least the softening temperature of the polymer or blends during the press lamination. If the layers are not oriented, the layers may be heated to a temperature between the softening temperature of the polymer or copolymer and up to 20° C. higher than the melting temperature of the polymer or copolymer. However, if the layers are oriented, the layers may only be heated to a temperature between the softening temperature of the polymer or copolymer and the de-orientation temperature of the polymer or copolymer, but no greater than the melting temperature of the polymer or copolymer. Notwithstanding this requirement, it has been found that if the layers have been annealed prior to lamination, the layers may be heated to a temperature between the softening temperature of the polymer or copolymer and a temperature 5° C. less than the annealing temperature of the polymer or copolymer. Annealing temperature for P4HB can be up to 85° C. and up to 200° C. for P4HB copolymers. The latter temperature may exceed the melting point of the polymer or copolymer. It is surprising that one can anneal at a temperature above the melting point of the polymer without the polymer melting, which was achieved by annealing an oriented film under tension. Provided the film is under tension when it is heated above its melting temperature to anneal it, the film will not melt. It is important, however, that any oriented layer not be subjected to a temperature that is more than 15° C. below its melt temperature before pressure is applied to the layer. In a preferred embodiment, the pressing platens are at ambient temperature, and the layers are heated after pressure has been applied, and not before.

In an alternative embodiment of press lamination, unoriented layers may be pre-heated (from the top, bottom or both sides), and then laminated while still hot in a press. If the layers are oriented, then the layers must be preferably constrained prior to heating, and the temperature must not exceed the de-orientation temperature of the layer. The layers may be heated by radiation heating, for example, with a ceramic heater. The pressing platens may be at ambient temperature, but are more preferably at or above the softening temperature of the polymer. This process may be automated and performed continuously.

The pressure applied during press lamination should be sufficient to ensure good bonding between the layers, but should not be so high that it causes compression of the layers. The pressure applied to the layers is at least 5 kPa, more preferably at least 50 kPa and more preferably at least 500 kPa.

A vacuum may be applied during lamination to avoid the formation of wrinkles in the layers and the entrapment of air bubbles during lamination. This is particularly desirable if the layers are very thin such as oriented films of P4HB.

The heating time required, and the length of time for press lamination, will depend among other factors upon the heating method selected, equipment set up, the pressure applied, and the number and thickness of the layers. However, a period of time necessary to heat the layers to at least the softening temperature of the polymers, and preferably higher, is the minimum amount of time required. The amount of time required to bond the layers together during press lamination can be between 1 second and 60 minutes, and more preferably between 1 minute and 30 minutes.

The laminates may also be produced directly by extrusion, co-extrusion and co-injection. For example, a layer of P4HB film may be laminated to another P4HB film, without application of pressure, by bringing the two films into contact while both films are still above the softening point of P4HB. This process may be run continuously, for example, by co-extrusion, or by extruding one film directly onto another film before it has cooled below its softening point.

The cooling time after lamination is preferably as short as possible, however, it must be of sufficient duration to allow the layers of the laminate to adequately bond so the product can be removed from the press without its integrity being compromised. The cooling time after lamination may be less than 15 minutes, more preferably less than 10 minutes.

The laminates may additionally be prepared using pressure sensitive adhesives (PSAs) and tackifiers. These adhesives may be used to reduce the contact pressure required to bond the layers together, and/or increase the adhesion between the layers. PSAs include acrylate copolymers, silicones, natural rubber, synthetic rubber, styrene block copolymers and polyurethanes, and may include tackifiers. Examples of tackifiers include aliphatic, cycloaliphatic and aromatic resins, terpene-phenol resins, rosins and their derivatives, terpenes and derivatives thereof, and hydrogenated hydrocarbon resins. The laminates may include degradable PSAs and/or tackifiers. EP 2647682 to Schümann et al. discloses biodegradable PSAs including amorphous compositions of polylactic acid and copolymers thereof. These compositions can include tackifiers and plasticizers, such as citrates, and can also be cross-linked. Other suitable degradable PSAs may include compositions based on epoxidized soybean oil, epoxidized soybean oil in combination with dihydroxyl soybean oil, poly(ethylene citrate), gluten, rapeseed oil, and medium chain length PHA polymers. The amount of PSA necessary to bond layers of the constructs, will depend upon the strength of the bond required. PSAs may be used to laminate layers of the constructs with a coating thickness of 10-200 g/m$^2$.

In a typical procedure for laminating layers of P4HB, copolymers and blends thereof, layers are stacked one on top of the other, and sandwiched between outer layers of a non-adherent material, such as PTFE sheets. This construct is then placed in a pneumatic press, such as a Carver press, and pressure applied prior to heating the platens. The pressure used to laminate the layers should be at least 5 kPa, more preferably greater than 50 kPa, and more preferably over 500 kPa, for a period of 2-15 minutes. Once pressure has been applied to the layers, the temperature of the platens can be raised to at least the softening temperature of the polymer. If the layers are oriented, the temperature of the platens should not exceed the de-orientation temperature of the polymer. If the layers are un-oriented, the temperature of the platens should not exceed 80° C. A preferred temperature for lamination of oriented P4HB layers, for example, is from 52-85° C. Once the temperature has been maintained for the desired time, the laminate is allowed time to cool and bond before being removed from the press.

Additional layers may be laminated with another laminate to make a multilayered or reinforced product.

These methods of lamination allow the preparation of highly oriented thick films of P4HB and copolymers thereof that are otherwise very difficult to manufacture by, for example, melt extrusion and orientation. This is because P4HB and copolymers thereof must be stretched many multiples of their original length in order to achieve significant orientation. For example, in order to make just a 200 μm biaxially oriented film of P4HB, an 8-10 mm thick un-oriented film of P4HB would be required, and it would need to be stretched seven times its original length.

IV. Medical Implants Made from Laminates of P4HB, Copolymer or Blends Thereof Applications of P4HB have been reviewed in Williams, et al., *Polyesters, III,* 4:91-127 (2002), Martin, et al., *Biochem. Eng. J.* 16:97-105 (2003). Medical devices and applications of P4HB have been disclosed by WO 00/56376 to Williams et al. Several patents including U.S. Pat. Nos. 6,555,123, 6,585,994, and 7,025,980 to Williams and Martin describe the use of PHAs in tissue repair and engineering. U.S. Pat. No. 8,034,270 to Martin et al., U.S. Pat. No. 8,016,883 to Coleman et al., U.S. Pat. No. 8,287,909 to Martin et al., WO 2011/119742 to Martin et al. and WO 2011/159784 to Cahil et al. disclose fibers, non-wovens, and textiles made by melt extrusion of P4HB. WO 2007/092417 to Rizk et al. discloses compositions of PLA (polylactic acid) toughened with P4HB suitable for medical applications.

U.S. Pat. No. 6,610,764 to Martin et al., and U.S. Pat. No. 6,548,569 to Williams et al. disclose vascular conduit scaffolds and heart valve scaffolds. These devices may be formed from a porous PGA nonwoven mesh coated with P4HB by using a strip to create an outer conduit, and folding a second strip within the conduit to form a tri-leaflet heart valve structure. The conduit is sealed, and the strips laminated together (i.e. attached) by applying heat at 75° C. from a heating iron. Although referred to as lamination, this process is more accurately described as welding. No pressure is used in this process to bond the layers together since the structure must remain porous for tissue in-growth. Rather the process is simply using heat at a temperature above the melting point of P4HB to melt the polymer and allow attachment between two surfaces. Laminates may be used in place of the welded materials, however.

WO 2012/142100 to Krishnaswamy discloses co-extrusion of PHA film and polyvinyl alcohol, and bonding of extruded layers using an adhesive, such as ethylene vinyl acetate copolymer resin grafted with maleic anhydride to form multi-layered films. European Patent No. 1539044 to Gingras discloses non-woven soft tissue implants, including implants made from polyhydroxyalkanoates that contain specific cell patterns. The description and examples disclose methods to laminate layers wherein one or two sides of one or more of the layers have already been developed for use as sealing layers. Examples include polypropylene coated with a sealant layer (i.e. AET Films AQS90), and a random copolymer of polypropylene that contains a high percentage of ethylene (i.e. Eltex® P KS409) that is designed for use as a sealing layer. These may be substituted with the laminates described herein.

Implants made from P4HB, copolymer and blends thereof, by lamination, have substantially improved properties for many medical applications relative to the same compositions made from brittle degradable thermoplastics. In particular, these implants have improved toughness that prevents breakage of the implant either during implantation or prior to the conclusion of healing. The implants may, for example, be made with a reduced profile decreasing the amount of material implanted, as well as facilitating the use of minimally invasive techniques of implantation. Lamination of layers of constructs made from P4HB, copolymers and blends thereof, also allows highly oriented implants of P4HB to be prepared which is particularly advantageous when orientation is necessary in more than one direction of the implant. The methods of lamination are also particularly advantageous in the formation of implants that include different layer constructions. For example, these methods can be used to laminate a film to a mesh. The latter can be used, for example, in hernia repair with the mesh providing strength and a matrix for tissue in-growth while the film side of the implant provides a barrier to tissue in-growth and prevents the formation of adhesions. The processes can also be used to prepare laminates that are partially or fully transparent. These implants are particularly desirable when it is necessary to be able to see through the implant (for example, during deployment).

Implants made from laminates including P4HB, copolymers and blends thereof, may be used for soft and hard tissue repair, regeneration, and replacement. Implants made from laminates of P4HB, copolymers and blends thereof, may be used in the following medical devices, including, but not limited to, wound healing device, bandage, patch, wound dressing, burn dressing, ulcer dressing, skin substitute, hemostat, tracheal reconstruction device, organ salvage device, pledgets, dural substitute, dural patch, nerve guide, nerve regeneration or repair device, hernia repair device, hernia mesh, hernia plug, device for temporary wound or tissue support, tissue engineering scaffold, guided tissue repair/regeneration device, laminated knitted, woven and non-woven meshes, fixation devices for meshes, anti-adhesion membrane, adhesion barrier, tissue separation membrane, retention membrane, sling, device for pelvic floor reconstruction, urethral suspension device, device for treatment of urinary incontinence, bladder repair device, bulking or filling device, bone marrow scaffold, clip, clamp, screw, pin, locking pin, nail, tube, medullary cavity nail, bone plate, interference screw, tack, arrow, fastener, rivet, staple, fixation device for an implant, bone graft substitute, bone void filler, suture anchor, bone anchor, ligament repair device, ligament augmentation device, ligament graft, anterior cruciate ligament repair device, tendon repair device, tendon graft, tendon augmentation device, rotator cuff repair device, meniscus repair device, meniscus regeneration device, articular cartilage repair device, osteochondral repair device, spinal fusion device, vertebral disc, device for treatment of osteoarthritis, stent, including coronary, cardiovascular, peripheral, ureteric, urethral, urology, gastroenterology, nasal, ocular, or neurology stents and stent coatings, stent graft, cardiovascular patch, catheter balloon, vascular closure device, intracardiac septal defect repair device, including but not limited to atrial septal defect repair devices and PFO (patent foramen ovale) closure devices, left atrial appendage (LAA) closure device, pericardial patch, vein valve, heart valve, vascular graft, myocardial regeneration device, periodontal mesh, guided tissue regeneration membrane for periodontal tissue, ocular cell implant, imaging device, cochlear implant, anastomosis device, cell seeded device, cell encapsulation device, controlled release device, drug delivery device, plastic surgery device, breast lift device, mastopexy device, breast reconstruction device, breast augmentation device (including devices for use with breast implants), breast reduction device (including devices for removal, reshaping and reorienting breast tissue), devices for breast reconstruction following mastectomy with or without breast implants, facial reconstructive device, forehead lift device, brow lift device, eyelid lift device, face lift device, rhytidectomy device, thread lift device (to lift and support sagging areas of the face, brow and neck), rhinoplasty device, device for malar augmentation, otoplasty device, neck lift device, mentoplasty device, cosmetic repair device, and device for facial scar revision.

The implants may be made directly in the lamination process, or a laminate may be produced that can be further processed into an implant. For example, machining, cutting, drilling, molding or thermoforming can all be used to form the implant. The laminates may be further processed using a laser to cut or drill the laminates. Non-porous laminates may be further processed into porous laminates. Preferably, highly oriented laminates are manufactured, and used directly as implants or after machining into implants. For example, implants that can be machined, cut, drilled, molded, or thermoformed from the laminates include, but are not limited to, wound healing devices, hernia repair devices, tissue engineering devices, guided tissue repair/regeneration devices, slings, devices for pelvic floor reconstruction, bone plates, wraps for ligament, tendon or nerve, breast lift devices, mastopexy devices, and devices for neck, face, eyelid, and brow lifts.

Oriented films of P4HB may be laminated and holes made in the laminate with a laser or drill. The diameter of the holes will depend upon the application. The holes may have a diameter between 1 μm and 5 mm. These perforated laminates may be used for hernia repair, mastopexy, and other lift procedures, including those of the breast, face, neck, eyebrow and eyelid. These perforated laminates are also desirable in plastic surgery and for laparoscopic delivery, since unlike, for example, knitted meshes, these perforated laminates have smooth surfaces. Since the surfaces of these laminates are smooth they are not visible under the surface of the body, and can be easily delivered in a minimally invasive manner. The perforated laminates have also been found to deploy (unroll) more easily after delivery in vivo than knitted meshes.

In some embodiments, laminated implants are made from layers of one or more films with one or more layers of fibers, meshes, non-woven textiles, woven textiles, braids, or molded forms. Films including P4HB, copolymers and blends thereof, may be laminated with fibers, meshes, non-woven textiles, woven textiles, braids, films or molded forms, for example, by extruding films directly onto these forms, or by stacking these layers in the desired manner and using a press with heated platens.

In other embodiments, a laminate of a P4HB film with a knitted monofilament P4HB mesh is prepared. The laminate may be made from a knitted monofilament P4HB mesh and a P4HB film wherein either or both of these components are oriented, and their orientation is not lost during lamination. Surprisingly good adhesion between the laminate components can be achieved when the lamination temperature is at or slightly above the softening temperature of the polymer, but below the de-orientation temperature of the polymer. It is surprising because it is usually necessary to add a sealant (glue) to make the layers stick together during lamination. Furthermore, these laminates can be prepared without any significant loss in the mechanical strength of the film or the oriented fibers of P4HB in the mesh, which is unexpected since exposure of the oriented polymer to elevated temperatures causes relaxation and loss of tensile properties.

The implants made from laminates of P4HB, copolymers and blends thereof, may incorporate bioactive agents. These agents may be added after lamination, or during subsequent processing of the laminates into implants. The bioactive agents may be added to the laminates and implants by any suitable means, including solvent solution coating, spray coating, powder coating, extrusion, latex coating, blending, plasma treatment, cross-linking, covalent bonding, and dip coating. The bioactive agents may also be combined with other polymers and additives, and then added to the implants. If necessary, primer coatings may first be added to the implants to improve adhesion of the bioactive agents. A topcoat, for example, of a polymer may also be applied to the implant to modify the release profile of a bioactive agent. In a preferred embodiment, bioactive agents are added to the implant using polymer solutions of P4HB and copolymers thereof.

The implants may be sterilized by any suitable method including ethylene oxide, gamma-irradiation, and electron-beam irradiation. A particularly preferred method of sterilization is the use of cold ethylene oxide.

The present invention will be further understood by reference to the following non-limiting examples.

EXAMPLE 1

Determination of Vicat Softening Point of P4HB

The Vicat softening point of a sample of poly-4-hydroxybutyrate was determined according to test method ASTM D1525-09 and found to be 51.9° C.

EXAMPLE 2

Preparation of Un-Oriented P4HB Films by Melt Extrusion

Dried pellets of P4HB, with a moisture content of less than 0.03% by weight, were fed into a 1.25 inch single screw extruder fitted with a 14 inch wide coat-hanger die with adjustable die lips initially set at a 60 μm gap. The heating zones were initially set at temperatures between 100° C. and 220° C., and the die temperature was set at 220° C. to 250° C. The polymer feed rate was 200 grams/hour, the extruder speed was 1.5 rpm, and the melt pressure was 1400 psi. A 3-roll stack with 12-inch roll diameter was used for casting, and the roll surface temperature was set at 18° C. The molten P4HB film exiting the die was cooled by casting it in an S-configuration over the rotating cast rollers and wound up with a take up roller to collect the un-oriented film. The thickness of the un-oriented film was 60 μm.

EXAMPLE 3

Biaxial Orientation of Un-Oriented P4HB Film

A P4HB film prepared using the method of Example 2 was biaxially oriented using a Bruckner Karo IV machine for monoaxial or biaxial stretching. Un-oriented film of 60 μm thickness was stretched 4× in the machine and cross directions to yield biaxially oriented film with an average thickness of 17 μm. Orientation resulted in an 88% increase in tensile strength of the film in the machine direction (to 166 MPa) and 58% in the cross direction (to 131 MPa). Elongation to break decreased about 84% in both the machine and cross directions during orientation. There was no change in molecular weight during orientation, but DSC revealed that the biaxially oriented film had a higher melting point of approximately 64° C. compared to a melting point of approximately 62° C. for the un-oriented film.

EXAMPLE 4

Lamination of Biaxially Oriented Films of P4HB Homopolymer

A biaxially oriented film of poly-4-hydroxybutyrate (P4HB) with a thickness of approximately 60 microns was cut into pieces measuring 2 in×2 in (5.08 cm×5.08 cm) using a pneumatic press. Two pieces of the P4HB film were placed together with one film on top of the other. The pieces of film were then placed between PTFE sheets, and laminated using a Carver press under a pressure of 1,650 psi (11.4 MPa). After pressure was applied to the film layers, the temperature was raised to 55° C., and maintained for 15 minutes.

The thickness of the film used in the lamination was measured, and found to be 59 microns. The thickness of the laminate made from two of these films was found to be 122 microns. The burst strength of the film was measured using a 3/8 in ball, and found to be 14.7 kgf. The burst strength of the laminate measured in the same manner was found to be 26.8 kgf. If one film has a burst strength of 14.7, two films might be expected to have a burst of 2×14.7=29.4. The fact that we measured 26.8 is very good because it means that the lamination process did not result in significant de-orientation of the films. If de-orientation of the films had occurred we would have measured a substantially lower burst for the laminate compared to bursting through two films. So, this example demonstrates that it is possible to stack and laminate, for example, ten 20 micron thick films and produce a laminated film with about the same burst strength as a biaxially oriented film of 200 micron thickness produced from an unoriented film that is about 8-10 mm thick. (Producing a biaxially oriented film of 200 micron thickness from a 8-10 mm thick film of P4HB would be technically very difficult as you would need to elongate the film about 7×.).

EXAMPLE 5

Lamination of Un-Oriented and Monoaxially Oriented Films of P4HB Homopolymer

Laminates may be prepared from un-oriented or monoaxially oriented P4HB films using substantially the same conditions as described in Example 4.

Modifications and variations of the disclosed compositions and methods of manufacture and use will be obvious to those skilled in the art from the foregoing and are intended to come within the scope of the following claims.

We claim:

1. A process for making a laminated structure comprising an oriented poly-4-hydroxybutyrate (P4HB) layer, the process comprising the steps of:
   (a) stacking two or more layers of construct for lamination, one on top of the other,
   wherein
      (i) the two or more layers of construct are selected from the group consisting of film with a thickness between 2 μm and less than 10 mm, sheet, tape, mesh, and woven and nonwoven fabrics; and
      (ii) one of the layers comprises oriented P4HB;
   (b) applying a pressure between 5-500 kPa, and subsequently heating the layers to a temperature between 52 and 85° C. to form a laminate; and
   (c) cooling the laminate before releasing the pressure from the laminate.

2. The process of claim 1 wherein two or more layers of construct in the laminated structure are oriented.

3. The process of claim 2 wherein the layers are selected from the group consisting of film, mesh, and woven and nonwoven fabrics.

4. The process of claim 3 wherein one layer, is mono- or bi-axially oriented, and optionally, wherein the layer is a film.

5. The process of claim 2 wherein the structure has one or more properties selected from the group consisting of tensile strength that is greater than 45 MPa, tensile modulus that is greater than 55 MPa, burst strength that is greater than 1 N, and elongation to break that is between 10% and 500%.

6. The process of claim 1 further comprising applying a tackifier prior to step (a).

7. The process of claim 3 wherein the two or more layers comprise knitted, woven or non-woven mesh made of P4HB and a film made of P4HB.

8. The process of claim 3 wherein one or more of the layers of construct are annealed prior to lamination.

9. The process of claim 8 wherein the one or more layers are annealed under tension.

10. The process of claim 1 wherein the laminated structure is cut, shaped, formed into a tube or plug, molded, thermoformed, stretched, or formed into an anatomical shape, three-dimensional shape, or asymmetric shape.

11. The process of claim 1 wherein the structure further comprises one or more polymers selected from the group consisting of poly(lactide); poly(glycolide); poly(lactide-co-glycolide); poly(lactic acid); poly(glycolic acid); poly(lactic acid-co-glycolic acid); polycaprolactone; poly(orthoester); polyanhydride; poly(phosphazene); polyhydroxyalkanoates; poly-3-hydroxybutyratepoly-3-hydroxybutyrate-co-3-hydroxyvalerate; P4HB copolymers; polyesters with one or more monomeric units selected from the group consisting of: glycolic acid, lactic acid; trimethylene carbonate, p-dioxanone and beta-caprolactone; poly(lactide-co-caprolactone); polycarbonate; tyrosine polycarbonate; synthetic and natural polyamides; polypeptides;-poly(amino acids); polyesteramide; poly(dioxanone); poly(alkylene alkylate); polyether; polyethylene glycol (PEG); polyethylene oxide;-polyvinyl pyrrolidone (PVP); polyurethane; polyetherester; polyacetal; polycyanoacrylate; poly(oxyethylene)/poly(oxypropylene) copolymer; polyketal; polyphosphate; phosphorous-containing polymer; polyphosphoester; polyalkylene oxalate; polyalkylene succinate; poly(maleic acid); chitin; chitosan; modified chitosan; collagen; silk; biocompatible polysaccharide; biocompatible block or random copolymers; hydrophilic or water soluble polymers; block polymers of PEG with one or more polymers selected from the group consisting of poly(lactide), poly(lactide-co-glycolide), and polycaprolactone; and block polymers of PVP with one or more polymers selected from the group consisting of poly(lactide), poly(lactide-co-glycolide) and polycaprolactone.

12. The process of claim 1 wherein the layers are laminated using press laminating, coextrusion, coinjection, or a continuous process.

13. The process of claim 1 wherein pressure sensitive adhesive is used to bond two or more of the layers together.

\* \* \* \* \*

UNITED STATES PATENT AND TRADEMARK OFFICE
CERTIFICATE OF CORRECTION

PATENT NO. : 11,154,642 B2  
APPLICATION NO. : 14/574649  
DATED : October 26, 2021  
INVENTOR(S) : Said Rizk et al.

Page 1 of 1

It is certified that error appears in the above-identified patent and that said Letters Patent is hereby corrected as shown below:

On the Title Page

In the Section "Related U.S. Application Data" please replace "61/920,870" with --61/920,970--

Signed and Sealed this  
Twenty-second Day of February, 2022

Drew Hirshfeld  
*Performing the Functions and Duties of the*  
*Under Secretary of Commerce for Intellectual Property and*  
*Director of the United States Patent and Trademark Office*